United States Patent [19]
Francotte et al.

[11] Patent Number: 4,778,895
[45] Date of Patent: Oct. 18, 1988

[54] 1-(6-PHENOXY-2-PYRIDYL)ETHANOL EMANTIOMERS AS PESTICIDES INTERMEDIATES

[75] Inventors: Eric Francotte, Kaiseraugst; Peter Ackermann, Pfeffingen, both of Switzerland

[73] Assignee: Ciba-Geigy Corporation, Ardsley, N.Y.

[21] Appl. No.: 36,144

[22] Filed: Apr. 6, 1987

Related U.S. Application Data

[63] Continuation of Ser. No. 676,964, Nov. 30, 1984, abandoned.

[30] Foreign Application Priority Data

Dec. 2, 1983 [CH] Switzerland ............ 6468/83
Nov. 9, 1984 [CH] Switzerland ............ 5388/84

[51] Int. Cl.⁴ ............... C07D 213/26; C07D 213/30
[52] U.S. Cl. ............................... 546/300; 546/296; 546/297; 546/301; 546/302
[58] Field of Search ............... 546/296, 297, 300, 301, 546/302

[56] References Cited

U.S. PATENT DOCUMENTS

| 4,163,787 | 8/1979 | Malhotra et al. | 514/351 |
| 4,226,872 | 10/1980 | Henrick | 514/345 |
| 4,238,614 | 12/1980 | Henrick | 546/301 |
| 4,323,574 | 4/1982 | Henrick | 514/345 |
| 4,393,213 | 7/1983 | Ozawa et al. | 546/298 |
| 4,499,275 | 2/1985 | Ozawa et al. | 546/298 |

OTHER PUBLICATIONS

Jacques et al., Enantiomers, Racemates and Resolutions, pp. 245-261, QD 481 J.3, 1981.
J. Organomet. Chem., 93, 253, 259, (1975).
Chromatographic, vol. 6, No. 6, (1973).
Chromatographia, vol. 6, Jun. 1973, pp. 277-280, Eline vollstandige Racemattrennug durch Elutions--Chromatographie an Cellulose-tri-acetat, (G. Hesse*/R. Hasel[1]).

Primary Examiner—Alan L. Rotman
Attorney, Agent, or Firm—Kevin T. Mansfield; Edward McC. Robert

[57] ABSTRACT

The invention relates to enantiomers of 1-(6-phenoxy-2-pyridyl)ethanols of the formula

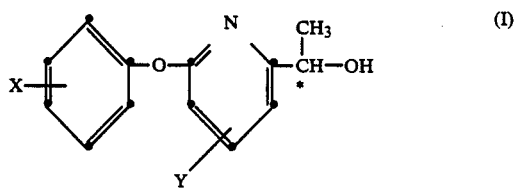

wherein * is (+) or (−) and X and Y are each independently of the other hydrogen, halogen, nitro, $C_1$-$C_4$alkyl, $C_1$-$C_4$haloalkyl, $C_1$-$C_4$alkoxy, $C_2$-$C_5$alkenyl or $C_2$-$C_5$alkynyl.

The invention also relates to the preparation of these enantiomers and to their use for the preparation of biocidal compounds.

6 Claims, No Drawings

1-(6-PHENOXY-2-PYRIDYL)ETHANOL EMANTIOMERS AS PESTICIDES INTERMEDIATES

This application is a continuation of application Ser. No. 676,964, filed Nov. 30, 1984, abandoned.

The present invention relates to novel enantiomers of 1-(6-phenoxy-2-pyridyl)ethanols, to the preparation thereof, and to the use thereof for synthesising biocidal compounds.

Specifically, the present invention relates to enantiomers of the formula

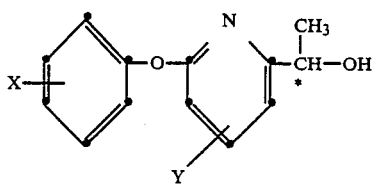
(I)

wherein * is (+) or (−) and X and Y are each independently of the other hydrogen, halogen, nitro, $C_1$–$C_4$alkyl, $C_1$–$C_4$haloalkyl, $C_1$–$C_4$-alkoxy, $C_2$–$C_5$alkenyl or $C_2$–$C_5$alkynyl.

Halogen in the above definition denotes fluorine, chlorine, bromine or iodine.

The suitable alkyl, haloalkyl, alkoxy, alkenyl or alkynyl groups for X and Y may be straight chain or branched. Examples of such groups are: methyl, methoxy, trifluoromethyl, ethyl, ethoxy, propyl, isopropyl, n-butyl, vinyl, 1-propenyl, ethynyl and 1-propynyl.

Preferred enantiomers of the formula I are those wherein * is (+) or (−), X is hydrogen, halogen, nitro or —C≡CH and Y is hydrogen.

Particularly preferred enantiomers of the formula I are those wherein * is (+) or (−), X is hydrogen or halogen and Y is hydrogen.

It is known that the enantiomers of formula I can be obtained by separating racemic 1-(6-phenoxy-2-pyridyl)ethanols on optically active carrier substances. The correct choice of carrier substance is essential for a successful separation. Surprisingly, it has now been found that racemic 1-(6-phenoxy-2-pyridyl)ethanols or their acetates can be separated into the enantiomers of the formula I by chromatography on microcrystalline celluloses, in particular on microcrystalline triacetyl celluloses as well as tribenzoyl celluloses.

Racemic 1-(6-phenoxy-2-pyridyl)ethanols are known (U.S. patent specification No. 4,323,574) or they can be prepared by known methods. Surprisingly, however, it is possible to prepare from the optically active alcohols of formula I, by reaction with acids customarily employed for pyrethroids, esters of stronger insecticidal and acaricidal activity than with the known racemic 1-(6-phenoxy-2-pyridyl)ethanols. The following acids can be used for example for the reaction with the enantiomeric 1-(6-phenoxy-2-pyridyl)ethanols of the formula I:

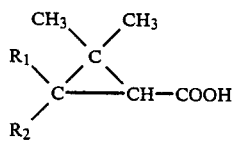
(a)

wherein
$R_1$ is hydrogen,
$R_2$ is

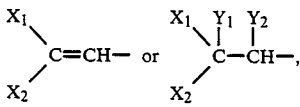

wherein
$X_1$ is methyl or halogen,
$X_2$ is methyl, trifluoromethyl, halogen or p-chlorophenyl,
$Y_1$ is halogen and
$Y_2$ is hydrogen or halogen.

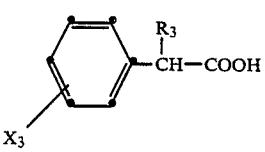
(b)

wherein
$X_3$ is hydrogen, halogen, $C_1$–$C_4$alkyl, $C_1$–$C_4$alkoxy, $C_1$–$C_4$haloalkyl, $C_1$–$C_4$haloalkoxy, —COCH$_3$ or methylenedioxy, and
$R_3$ is isopropyl or cyclopropyl.

EXAMPLE 1

Preparation of the enantiomers by chromatographic separation of the racemic alcohol of the formula

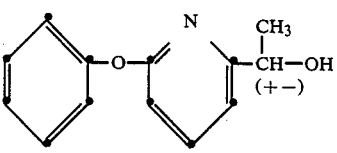

A glass column (1.25 cm × 58.5 cm) is filled with 36 g of triacetyl cellulose [preparation by known methods: Chromatographia 6, 277 (1973)] and a 95:5 mixture of ethanol/water. 6.5 g of the racemate of the formula

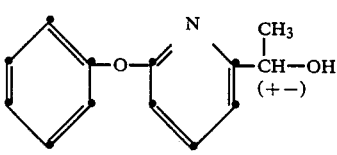

are applied to and chromatographed on this carrier.

The racemate is chromatographed with ethanol/water (95:5) under a pressure of 13 bar at a rate of flow of 24 ml/h. The eluate is passed through flow cuvettes of a polarimeter (Perkin-Elmer 241 MC) and a UV spectrophotometer (Shimadzu UV-120-02). A two-channel recorder registers substance concentration and angle of rotation.

The angles of rotation of the two enantiomers are calculated from the elution curve.

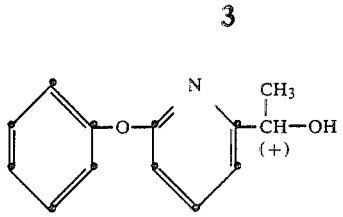

$[\alpha]_{365} = +89° \pm 2°$
(c = 0.033; ethanol/H$_2$O 95:5)

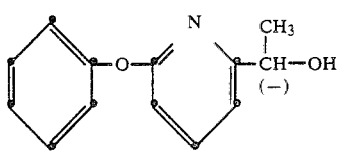

$[\alpha]_{365} = -91° \pm 2°$
(c = 0.042; ethanol/H$_2$ 95:5)

separation factor $$\alpha = \frac{V_2 - V_0}{V_1 - V_0} = 1.25$$

EXAMPLE 2

Preparation of the enantiomers by chromatographic separation of the racemic alcohol of the formula

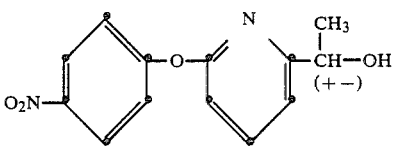

The racemate is chromatographed through a column of tribenzoyl cellulose (0.4 cm×25 cm) with a 9:1 mixture of hexane/isopropanol at a rate of flow of 0.2 ml/min.

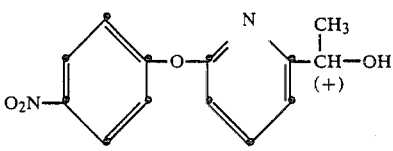

separation factor = 1.15
$R_s$ = resolution factor = 1.0

EXAMPLE 3

Preparation of the enantiomers of the racemic alcohol of the formula

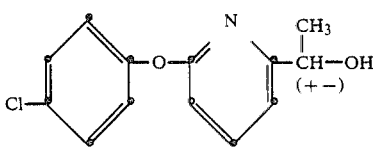

(a) Chromatographic separation of the racemates of the acetate.

20 mg of the racemic acetate are chromatographed through a column of triacetyl cellulose (1.25 cm×30 cm; 14 g of triacetyl cellulose) eluted with a 95:5 mixture of ethanol/water a rate of flow of 33 ml/h. The angles of rotation of both acetate enantiomers are measured.

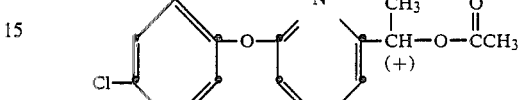

$[\alpha]_{436} = +77° \pm 3°$
(c = 0.38; ethanol)

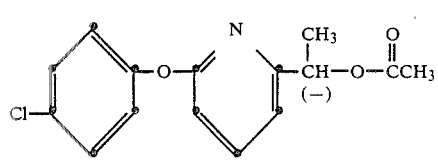

$[\alpha]_{436} = -76° \pm 3°$
(c = 0.38; ethanol)

separation factor = 7.9

(b) Saponification of the acetates 5 mg of the optically pure (+) and (−) acetate (Example 3a) and 15 mg of K$_2$CO$_3$ are refluxed for 1 hour in 0.3 ml of a 10:7 mixture of ethanol/water. The mixture is diluted with 3 ml of chloroform and dried over sodium sulfate. After filtration and evaporation of the solution, the residue is purified by chromatography over silica gel (eluant: chloroform), affording the enantiomers of the formulae

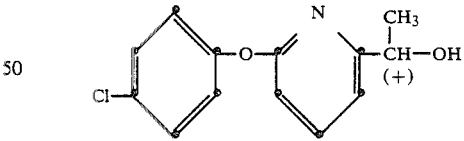

$[\alpha]_{436} = +48° \pm 3°$
(c = 0.23; ethanol)

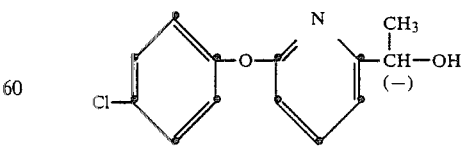

$[\alpha]_{436} = -45° \pm 3°$
(c = 0.21; ethanol)

The following acetate and alcohol enantiomers are also obtained in corresponding manner:

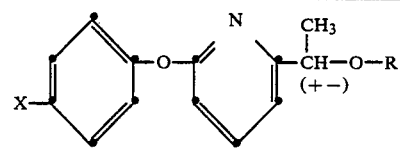

| X | Separation factor | R=CCH₃ [α]₄₃₆ (ethanol) | R=H [α]₄₃₆ (ethanol) |
|---|---|---|---|
| F | 1,36 | +96° ± 3° (C = 0.41) | +54° ± 3° (C = 0.30) |
|  |  | −99° ± 3° (C = 0.53) | −51° ± 3° (C = 0.39) |
| Br | 1,80 | +72° ± 3° (C = 0.85) | +48° ± 3° (C = 0.74) |
|  |  | −71° ± 3° (C = 0.96) | −49° ± 3° (C = 0.79) |
| —C≡CH | 1,87 | +91° ± 3° (C = 0.65) | +72° ± 3° (C = 0.71) |
|  |  | −91° ± 3° (C = 0.97) | −77° ± 3° (C = 0.54) |

EXAMPLE 4

Preparation of R-α-methyl-(6-phenoxy-2-picolyl) 1-R-cis-3-(2,2-dichlorovinyl)-2,2-dimethylcyclopropanecarboxylate To an ice-cooled solution of 3.2 g of 1-R-cis-3-(2,2-dichlorovinyl)-2,2-dimethylcyclopropanecarboxylic acid chloride in 20 ml of toluene are added, in succession, a solution of 1.4 g of pyridine in 5 ml of toluene and then 3 g of the compound of the formula

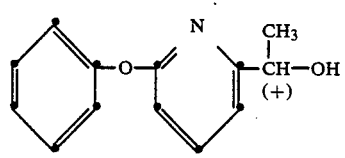

in 10 ml of toluene. Then 200 mg of 4-dimethylaminopyridine are added to the slightly yellowish suspension and the reaction mixture is stirred for 16 hours at room temperature. After addition of 100 ml of toluene, the organic phase is washed with ice-cooled 1N HCl, 10% K₂CO₃, saturated NaHCO₃, and a saturated solution of NaCl, and dried over MgSO₄. The solvent is then removed under reduced pressure and the crude product is purified over silica gel with toluene as eluant, affording R-α-methyl-(6-phenoxy-2-picolyl) 1-R-cis-3-(2,2-dichlorovinyl)-2,2-dimethylcyclopropanecarboxylate (compound 1) with the following physical data:

$n_D^{20°} = 1.5605$ $[\alpha]_D = +116° \pm 1° [c = 1.07 \text{ in benzene}]$

The following esters are also prepared in analogous manner:

(2) S-α-methyl-(6-phenoxy-2-picolyl) 1-R-cis-3-(2,2-dichlorovinyl)-2,2-dimethylcyclopropanecarboxylate $n_D^{20°} = 1.5591$ $[\alpha]_D = -69° \pm 1° [c = 0.937 \text{ in benzene}]$ (3) R-α-methyl-6-(6-phenoxy-2-picolyl) 1-R-trans-3-(2,2-dichlorovinyl)-2,2-dimethylcyclopropanecarboxylate $n_D^{20°} = 1.5581$ $[\alpha]_D = +77° \pm 1° [c = 0.74 \text{ in benzene}]$ (4) S-α-methyl-(6-phenoxy-2-picolyl) 1-R-trans-3-(2,2-dichlorovinyl)-2,2-dimethylcyclopropanecarboxylate $n_D^{21°} = 1.5581$ $[\alpha]_D = -56° \pm 1° [c = 0.83 \text{ in benzene}]$

EXAMPLE 5

Insecticidal stomach poison action

Cotton plants are sprayed with a test solution containing 1.25 g, 0.6 g or 0.3 g of a compound of Example 4 per 100 l of H₂O. After the spray coating has dried, the plants are populated with larvae of the species Heliothis virescens (L₁ stage). Two plants are used for each test compound and test species and a mortality count is made after 24 and 48 hours. The test is carried out at 24° C. and 60% relative humidity.

The activity of compound 1 of Example 4 against larvae of the species Heliothis virescens is shown in the following table:

Percentage mortality of Heliothis virescens L₁ larvae

|  | 1.25 g | | 0.6 g | | 0.3 g conc. | |
|---|---|---|---|---|---|---|
|  | 24 | 48 | 24 | 48 | 24 | 48 h |
| Compound 1 of Example 4 | 43 | 90 | 43 | 77 | 28 | 55 |
| mixture of isomers of formula* known from U.S. Pat. No. 4,323,574 | 15 | 20 | 0 | 0 | 0 | 0 |

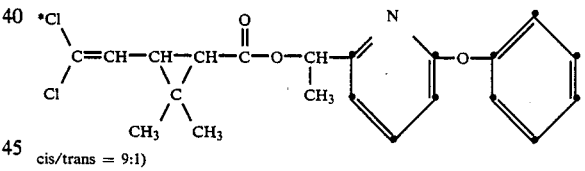

cis/trans = 9:1)

What is claimed is:

1. An enantiomer of the formula

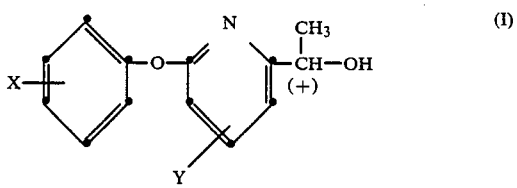

wherein X is hydrogen, halogen, nitro, C₁–C₄alkyl, C₁–C₄haloalkyl, C₁–C₄alkoxy, C₂–C₅alkenyl or C₂–C₅alkynyl and Y is hydrogen.

2. An enantiomer according to claim 1, wherein X is hydrogen, halogen, nitro or —C≡CH and Y is hydrogen.

3. An enantiomer according to claim 2, wherein X is hydrogen or halogen and Y is hydrogen.

4. The enantiomer according to claim 3 of the formula

5. The enantiomer according to claim 3 of the formula
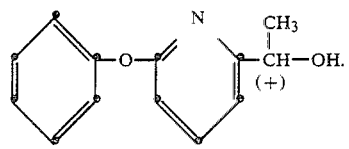
6. The enantiomer according to claim 2 of the formula
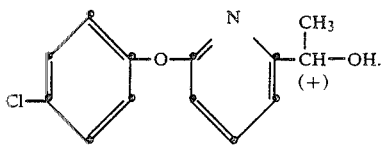
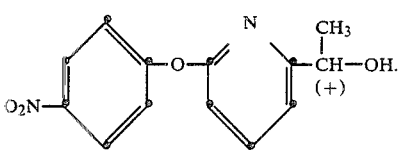
* * * * *